US012588830B1

(12) United States Patent
Liu et al.

(10) Patent No.: US 12,588,830 B1
(45) Date of Patent: Mar. 31, 2026

(54) ELECTRONIC DEVICES WITH BREATH SENSING SYSTEMS

(71) Applicant: Apple Inc., Cupertino, CA (US)

(72) Inventors: Sheng Liu, San Jose, CA (US); Mahdi Nezamabadi, San Jose, CA (US); Vrinda Thareja, San Jose, CA (US); Serhan O Isikman, Redwood City, CA (US)

(73) Assignee: Apple Inc., Cupertino, CA (US)

( * ) Notice: Subject to any disclaimer, the term of this patent is extended or adjusted under 35 U.S.C. 154(b) by 747 days.

(21) Appl. No.: 17/947,014

(22) Filed: Sep. 16, 2022

Related U.S. Application Data

(60) Provisional application No. 63/247,782, filed on Sep. 23, 2021.

(51) Int. Cl.
*A61B 5/08* (2006.01)
*G01N 21/3518* (2014.01)
*G16H 40/67* (2018.01)

(52) U.S. Cl.
CPC ......... *A61B 5/082* (2013.01); *G01N 21/3518* (2013.01); *G16H 40/67* (2018.01)

(58) Field of Classification Search
None
See application file for complete search history.

(56) References Cited

U.S. PATENT DOCUMENTS 8,280,436 B2 * 10/2012 Harris, Jr. ............... H04M 1/21
340/576
9,562,915 B2 2/2017 Burgi et al.

11,103,157 B2 8/2021 Gupta et al.
2004/0081582 A1 4/2004 Brooke
2008/0009688 A1 * 1/2008 Dahlen ............... A61B 5/1455
600/310
2013/0023782 A1 * 1/2013 Karlsson ............. G01N 21/643
600/532
2013/0079658 A1 * 3/2013 Cardoso ............. G01N 33/497
600/532
2014/0171759 A1 * 6/2014 White ................. A61B 5/6835
600/306

(Continued)

FOREIGN PATENT DOCUMENTS

EP 2796872 B1 3/2017

*Primary Examiner* — John R Downey
(74) *Attorney, Agent, or Firm* — Treyz Law Group, P.C.; Kendall P. Woodruff

(57) ABSTRACT

An electronic device may include sensors such as a breath sensor. The breath sensor may be aligned with a sensor window in the housing and may be configured to gather breath measurements through the sensor window without the use of a mouthpiece. The breath sensor may be a non-dispersive infrared breath sensor having an infrared light source and an infrared light detector. The infrared light source may emit infrared light through the sensor window and the infrared light detector may detect the infrared light after it passes through a volume of breath containing a target gas molecule that serves as a biomarker for a given health condition. Control circuitry in the electronic device may analyze the breath measurements to determine a concentration of the target gas molecule and may compare the concentration with database information to determine whether a user has the given health condition.

15 Claims, 11 Drawing Sheets

(56) References Cited

U.S. PATENT DOCUMENTS

| | | | |
|---|---|---|---|
| 2015/0045641 A1* | 2/2015 | Rule | A61B 5/150229 |
| | | | 600/347 |
| 2015/0141073 A1* | 5/2015 | Shen | H04M 1/21 |
| | | | 73/23.3 |
| 2019/0120821 A1 | 4/2019 | Atsalakis | |
| 2019/0167176 A1 | 6/2019 | Annoni et al. | |
| 2019/0200899 A1* | 7/2019 | Yoshida | A61B 5/097 |
| 2020/0196977 A1 | 6/2020 | Martin et al. | |
| 2021/0041291 A1* | 2/2021 | Liu | G01J 3/108 |
| 2021/0361242 A1 | 11/2021 | Elliott et al. | |
| 2022/0007950 A1* | 1/2022 | Lev | A61B 5/7267 |

* cited by examiner

ELECTRONIC DEVICES WITH BREATH SENSING SYSTEMS

This application claims the benefit of provisional patent application No. 63/247,782, filed Sep. 23, 2021, which is hereby incorporated by reference herein in its entirety.

BACKGROUND

This relates generally to electronic devices and, more particularly, to electronic devices with sensors.

Electronic devices may include sensors. For example, a cellular telephone may have optical sensors for measuring ambient light levels and for monitoring whether a user's head or other body part is in close proximity to the cellular telephone. A cellular telephone may also have a camera for capturing images.

Challenges can arise when using sensors in an electronic device. If care is not taken, the sensor data may be difficult to gather or may be insufficient to provide a user with desired functionality.

SUMMARY

An electronic device such as a portable electronic device may be provided with sensors such as a breath sensor. The breath sensor may be aligned with a sensor window in the housing and may be configured to gather breath measurements through the sensor window without the use of a mouthpiece.

The breath sensor may be a non-dispersive infrared breath sensor having an infrared light source and an infrared light detector. The infrared light source may emit infrared light through the sensor window and the infrared light detector may detect the infrared light after it passes through a volume of breath containing a target gas molecule that serves as a biomarker for a given health condition. Control circuitry in the electronic device may analyze the breath measurements to determine a concentration of the target gas molecule and may compare the concentration with database information to determine whether a user has the given health condition.

Control circuitry may use a proximity sensor to gather distance information such as a distance between the breath sensor and the user's mouth or nose. This information may be used to determine a path length traveled by infrared light as it travels through the breath and back to the breath sensor. This path length information, as well as the intensity of light emitted by the light source, the intensity of light detected by the light detector, and the molar attenuation coefficient of the target gas molecule, may be used to determine the concentration of the target gas molecule in the user's breath.

Other sensors such as a visible light camera and/or an infrared depth sensing camera may be used to capture images of the user's face. Control circuitry may analyze the captured images to determine an appropriate target for breath sensing measurements (e.g., the nose or the back of the inside of the user's mouth). The control circuitry may adjust a beam steerer in the breath sensor so that the infrared light beam is directed towards the appropriate location on the user's face.

DETAILED DESCRIPTION

Electronic devices may include one or more breath sensors such as photoacoustic sensors, non-dispersive infrared sensors, and/or other suitable types of sensors for detecting concentrations of different molecules in a volume of gas. A breath sensor in an electronic device may be used to analyze a user's breath in free space and/or in the user's mouth (e.g., without requiring a nozzle, mouth pipe, other mouthpiece, etc.). During breath analysis, control circuitry within the electronic device may analyze sensor data from the breath sensor to determine the concentration of one or more target gas molecules (e.g., acetone, carbon dioxide, ammonia, nitric oxide, etc.) in the user's breath. The control circuitry may compare the breath information (e.g., breath information such as the concentration of one or more target gas molecules detected in the user's breath) with database information to characterize the user's breath. For example, control circuitry may compare the measured breath information with database information that correlates concentration levels of breath gases with different health conditions (e.g., diabetes, high cholesterol, other diseases, other health conditions, etc.). The control circuitry may output a breath analysis result based on how the user's breath information compares with the database information.

After analyzing the acquired breath sensor data, control circuitry in the electronic device can take action in response to the analysis results. For example, if an abnormal condition (e.g., a high concentration of acetone in the user's breath, which may indicate a risk for diabetes) is detected, notifications can be issued, databases can be updated, recommendations may be provided, and/or other actions may be taken based on the breath sensor analysis.

Figure 1:
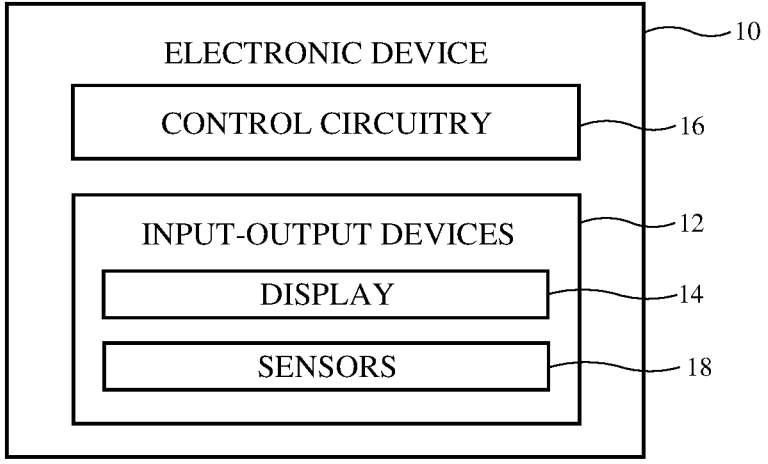
FIG. 1 is a schematic diagram of an illustrative electronic device with a breath sensor in accordance with an embodiment.

FIG. 1 is a schematic diagram of an illustrative electronic device with one or more breath sensors. Electronic device 10 of FIG. 1 may be a computing device such as a laptop computer, a computer monitor containing an embedded computer, a tablet computer, a cellular telephone, a media player, or other handheld or portable electronic device, a smaller device such as a wristwatch or other device worn on a user's wrist, a pendant device, a headphone or earpiece device, a head-mounted device such as eyeglasses, goggles, or other equipment worn on a user's head, or other wearable or miniature device, a television, a computer display that does not contain an embedded computer, a gaming device, a navigation device, an embedded system such as a system in which electronic equipment with a display is mounted in a kiosk or automobile, equipment that implements the functionality of two or more of these devices, or other electronic equipment. Illustrative configurations in which device 10 is a portable device such as a wristwatch, cellular telephone, or tablet computer and, more particularly, a portable device that is water resistant or waterproof may sometimes be described herein as an example.

As shown in FIG. 1, electronic device 10 may have control circuitry 16. Control circuitry 16 may include storage and processing circuitry for supporting the operation of device 10. The storage and processing circuitry may include storage such as hard disk drive storage, nonvolatile memory (e.g., flash memory or other electrically-programmable-read-only memory configured to form a solid state drive), volatile memory (e.g., static or dynamic random-access-memory), etc. Processing circuitry in control circuitry 16 may be used to control the operation of device 10. The processing circuitry may be based on one or more microprocessors, microcontrollers, digital signal processors, baseband processors, power management units, audio chips, application specific integrated circuits, etc. Control circuitry 16 may include communications circuitry for supporting wired and/or wireless communications between device 10 and external equipment. For example, control circuitry 16 may include wireless communications circuitry such as cellular telephone communications circuitry and wireless local area network communications circuitry.

Input-output circuitry in device 10 such as input-output devices 12 may be used to allow data to be supplied to device 10 and to allow data to be provided from device 10 to external devices. Input-output devices 12 may include buttons, joysticks, scrolling wheels, touch pads, key pads, keyboards, microphones, speakers, tone generators, haptic output devices, cameras, light-emitting diodes and other status indicators, data ports, etc. A user can control the operation of device 10 by supplying commands through input-output devices 12 and may receive status information and other output from device 10 using the output resources of input-output devices 12.

Input-output devices 12 may include one or more displays such as display 14. Display 14 may be an organic light-emitting diode display, a display formed from an array of crystalline semiconductor light-emitting diode dies, a liquid crystal display, or other display. Display 14 may be a touch screen display that includes an touch sensor for gathering touch input from a user. Touch sensors may be formed from an array of capacitive touch sensor electrodes, acoustic touch sensor structures, resistive touch components, force-based touch sensor structures, light-based touch sensor structures, or other suitable touch sensor arrangements.

As shown in FIG. 1, input-output devices 12 may include sensors 18. Sensors 18 may include gas sensors (e.g., gas sensors for analyzing gases in the environment and/or gas sensors that form breath sensors for analyzing gases in a user's breath), capacitive sensors, light-based proximity sensors, magnetic sensors, accelerometers, force sensors, touch sensors, temperature sensors, pressure sensors, inertial measurement units, accelerometers, gyroscopes, compasses, microphones, radio-frequency sensors, three-dimensional image sensors (e.g., structured light sensors with light emitters such as infrared light emitters configured to emit structured light and corresponding infrared image sensors, three-dimensional sensors based on pairs of two-dimensional image sensors, etc.), cameras (e.g., visible light cameras and/or infrared light cameras), light-based position sensors (e.g., lidar sensors), monochrome and/or color ambient light sensors, and other sensors. Sensors 18 such as ambient light sensors, image sensors, optical proximity sensors, lidar sensors, optical touch sensors, and other sensors that use light and/or components that emit light such as status indicator lights and other light-emitting components may sometimes be referred to as optical components.

Figure 2:
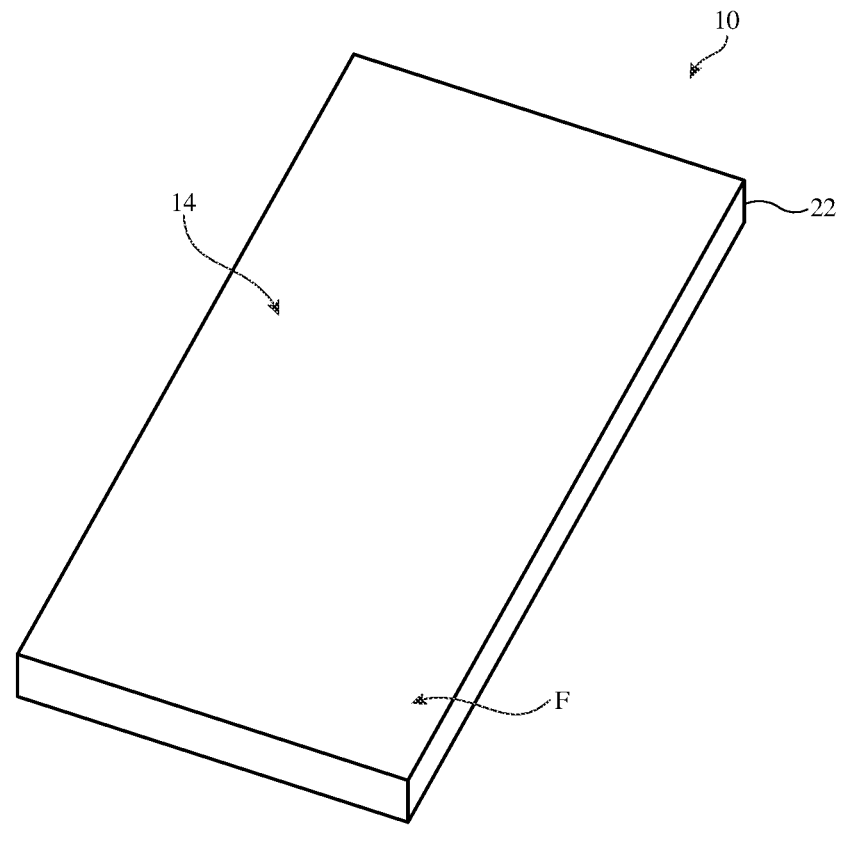
FIG. 2 is a perspective view of an illustrative electronic device with a breath sensor in accordance with an embodiment.

A perspective view of an illustrative electronic device of the type that may include a breath sensor is shown in FIG. 2. In the example of FIG. 2, device 10 includes a display such as display 14 mounted in housing 22. Display 14 may be a liquid crystal display, a light-emitting diode display such as an organic light-emitting diode display or a display formed from crystalline semiconductor light-emitting diode dies, or other suitable display. Display 14 may have an array of image pixels extending across some or all of front face F of device 10 and/or other external device surfaces. The array of image pixels may be rectangular or may have other suitable shapes. Display 14 may be protected using a display cover layer (e.g., a transparent front housing layer) such as a layer of transparent glass, clear plastic, sapphire, or other clear layer. The display cover layer may overlap the array of image pixels.

Housing 22, which may sometimes be referred to as an enclosure or case, may be formed of plastic, glass, ceramics, fiber composites, metal (e.g., stainless steel, aluminum, etc.), other suitable materials, or a combination of any two or more of these materials. Housing 22 may be formed using a unibody configuration in which some or all of housing 22 is machined or molded as a single structure or may be formed using multiple structures (e.g., an internal frame structure, one or more structures that form exterior housing surfaces, etc.). If desired, a strap may be coupled to a main portion of housing 22 (e.g., in configurations in which device 10 is a wristwatch or head-mounted device).

Figure 3:
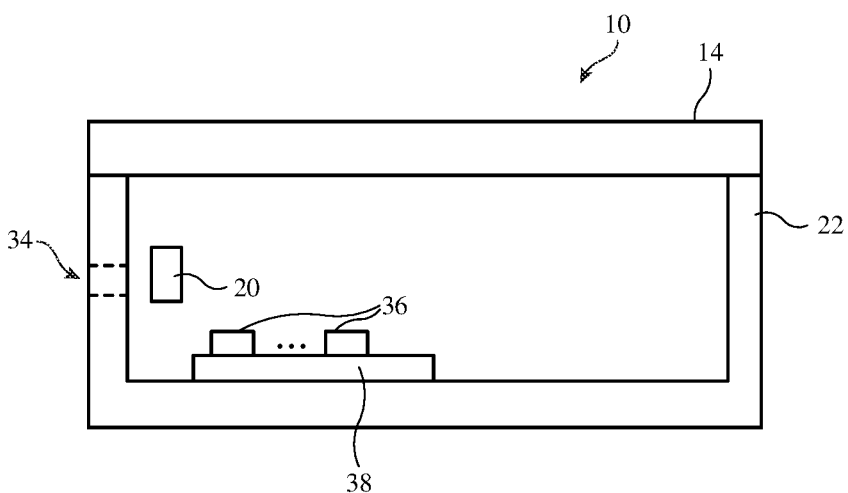
FIG. 3 is a cross-sectional side view of an illustrative electronic device with a breath sensor in accordance with an embodiment.

As shown in the cross-sectional side view of FIG. 3, internal electrical components 36 (e.g., integrated circuits, discrete components, etc.) for forming control circuitry 16 and input-output devices 12 may be mounted in the interior of housing 22 (e.g., on one or more substrates such as printed circuit 38). In some configurations, components 36 may be attached to display 14 (e.g., circuitry may be mounted to the surface of display 14).

As shown in FIG. 3, housing 22 may have one or more sensor windows 34. Sensor windows such as window 34 may be formed in a sidewall of housing 22, a front wall of housing 22, and/or a rear wall of housing 22. Sensor windows in housing 22 such as window 34 may include gas-transparent windows, optically transparent windows, acoustically transparent windows, and/or windows that are transparent to other types of signals to be detected by a sensor in device 10. In arrangements where a sensor window in housing 22 is for an optical sensor in device 10 (e.g., a proximity sensor, camera, infrared image sensor, ambient light sensor, etc.), the sensor window may be optically transparent. An optically transparent window may include a transparent window member formed from sapphire or other crystalline material, glass, and/or clear polymer and may be mounted in an opening in a metal housing wall or other opaque housing wall. Optical sensor windows may also be formed from perforations or other openings in a housing wall that allow light to pass.

In arrangements where a sensor window in housing 22 is for an acoustic sensor or breath sensor, the sensor window may be formed from one or more openings (e.g., perforations) in a housing wall that are transparent to gas and/or acoustic waves (e.g., sound). As shown in FIG. 3, for example, a breath sensor such as breath sensor 20 may be mounted behind sensor window 34. Window 34 may be a single opening, two or more openings, and/or an array of perforations that allow gas molecules to enter and exit device 10 through gas sensor window 34.

Breath sensor 20 (sometimes referred to as gas sensor 20, breath analysis sensor 20, non-dispersive infrared sensor 20, photoacoustic sensor 20, etc.) may be formed from one or more gas sensors such as non-dispersive infrared gas sensors, photoacoustic-based gas sensors, and/or other gas sensors configured to measure a concentration of one or more target gas molecules in a user's breath. Breath sensor 20 may analyze gas molecule concentrations in a volume of gas in free space and/or within a contained volume such as the user's mouth, without requiring a nozzle, mouthpiece, or other enclosed chamber.

During breath sensor analysis, a user may breath onto device 10 in the vicinity of window 34. Gas molecules in the user's breath may be detected by breath sensor 20. Breath sensor 20 may be configured to detect a concentration of one or more target gas molecules such as acetone, carbon dioxide, ammonia, nitric oxide, and/or other suitable target gas molecules in the user's breath. Different gas molecules in the breath may serve as biomarkers for different diseases and/or other health conditions. For example, carbon dioxide in the breath may be a biomarker for a metabolic disorder; acetone in the breath may be a biomarker for diabetes; ammonia may be a biomarker for chronic kidney disease; and nitric oxide may be a biomarker for asthma. These are merely illustrative examples. Other gas molecules may serve as biomarkers for other types of diseases or other health conditions.

Control circuitry 16 in device 10 may analyze breath sensor measurements from breath sensor 20 and may take suitable action based on the analysis results. For example, control circuitry 16 may compare the concentration of one or more gas molecules in the user's breath with database information that correlates concentration levels of breath gases with different health conditions (e.g., diabetes, high cholesterol, other diseases, dehydration, other health conditions, etc.). The control circuitry may output a breath analysis result based on how the user's breath information compares with the database information, which may include providing a visual notification on display 14, providing an audio notification via one or more speakers in device 10, providing a haptic notification via one or more haptic output devices in device 10, updating a health-related application on device 10, logging the breath analysis results in a health-related application on device 10, transmitting the breath analysis results to an external electronic device and/or to a cloud-based location, providing recommendations, and/or taking other suitable actions. For example, if excess levels of acetone are detected in a user's breath, the user may be notified that the user is at risk of diabetes and should consult with a physician.

Figure 4:
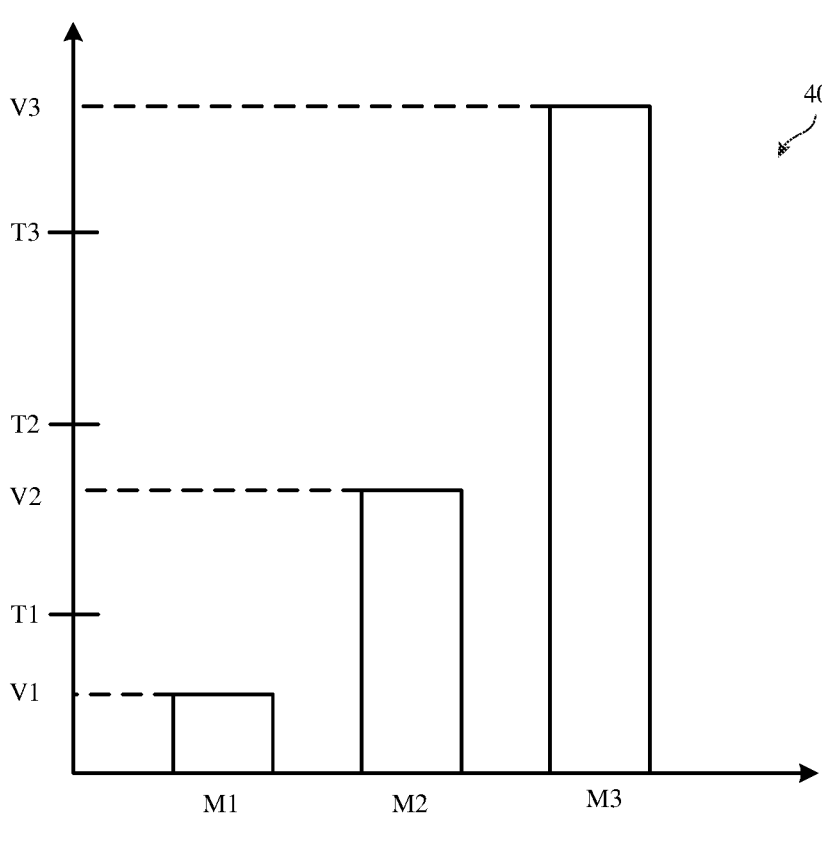
FIG. 4 is a chart showing illustrative breath analysis results in accordance with an embodiment.

FIG. 4 is a chart showing illustrative breath sensor data that may be produced based on the breath sensor measurements captured with breath sensor 20. Breath sensor data 40 may include concentration levels of various target gas molecules such as gas molecules M1, M2, and M3. Molecules M1, M2, and M3 may serve as biomarkers for different diseases or other health conditions (e.g., diabetes, high cholesterol, other diseases, dehydration, other health conditions, etc.). Breath sensor data 40 may be based on one or more measurements of a user's breath, taken at the same time and/or taken at different times. If desired, breath sensor 20 may measure the concentration of a given gas molecule multiple times and the resulting measurements may be averaged to produce a single concentration value.

In the example of FIG. 4, breath sensor 20 detects concentration level V1 of molecule M1, concentration level V2 of molecule M2, and concentration level V3 of molecule M3 in the user's breath. Control circuitry 16 may compare the concentration levels of the target gas molecules with database information (e.g., database information stored in device 10 and/or database information retrieved from the internet) to determine whether the concentration levels of the target gas molecules in the breath are normal (e.g., healthy) or abnormal (e.g., indicating a risk of disease, dehydration, or other potentially unhealthy conditions). For example, if M1 serves as a biomarker for a first health condition (e.g., diabetes), the database information may indicate that concentration levels of molecule M1 in the breath above threshold T1 indicate a presence of the first health condition, while concentration levels of molecule M1 in the breath below threshold T1 indicate an absence of the first health condition. If M2 serves as a biomarker for a second health condition (e.g., dehydration), the database information may indicate that concentration levels of molecule M2 in the breath above threshold T2 indicate a presence of the second health condition, while concentration levels of molecule M2 in the breath below threshold T2 indicate an absence of the second health condition. If M3 serves as a biomarker for a third health condition (e.g., a metabolic disorder), the database information may indicate that concentration levels of molecule M3 in the breath above threshold T3 indicate a presence of the third health condition while concentration levels of molecule M3 in the breath below threshold T3 indicate an absence of the third health condition.

Using the database information, control circuitry 16 may compare measured concentration level V1 of molecule M1 with threshold T1 to determine whether the user has a first health condition; may compare measured concentration level V2 of molecule M2 with threshold T2 to determine if the user has a second health condition; and may compare measured concentration level V3 of molecule M3 with threshold T3 to determine if the user has a third health condition. Detecting three different molecules is merely illustrative, however. If desired, breath sensor 20 may be used to detect a single type of gas molecule, two types of gas molecules, more than three types of gas molecules, or any other suitable number of gas molecules depending on the target health conditions that breath sensor 20 is used to detect.

Gas sensor 20 may be a spectroscopic sensor that detects target gases by illuminating the target gases with infrared light. When the energy level of the infrared light is equivalent to the natural frequency of a gas molecule, the gas molecule will absorb the infrared light, resulting in molecular vibration. In some arrangements, gas sensor 20 may include an infrared emitter that emits light at a target wavelength and an infrared detector that detects an amount of transmitted infrared light after the infrared light passes through a volume of breath containing the target gas molecules. Control circuitry 16 may then calculate a concentration of the target gas molecule according to the Lambert-Beer Law. In other arrangements, gas sensor 20 may include an infrared emitter that emits light at a target wavelength and an acoustic sensor (e.g., a microphone) that detects a resulting vibration as the target gas molecules absorb the infrared light. Control circuitry 16 may then determine a concentration of the target gas molecule based on the vibration detected by the acoustic sensor. These examples are merely illustrative, however. If desired, sensor 20 may be based on other gas sensing technologies.

Figure 5:
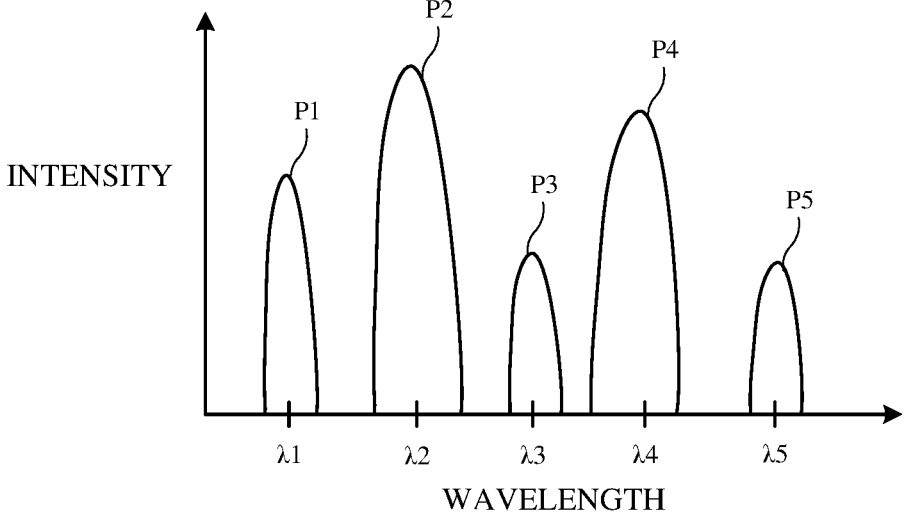
FIG. 5 is a graph showing illustrative absorption spectra for different gas molecules that may serve as biomarkers for various health conditions in accordance with an embodiment.

FIG. 5 is a graph showing illustrative absorption spectra of various target gas molecules that may serve as biomarkers for different health conditions. For example, curve P1 indicates that the absorption line for a first target gas molecule centers around wavelength $\lambda 1$; curve P2 indicates that the absorption line for a second target gas molecule centers around wavelength $\lambda 2$; curve P3 indicates that the absorption line for a third target gas molecule centers around wavelength $\lambda 3$; curve P4 indicates that the absorption line for a fourth target gas molecule centers around wavelength $\lambda 4$; and curve P5 indicates that the absorption line for a fifth target gas molecule centers around wavelength $\lambda 5$. When it is desired to detect the first target gas molecule, breath sensor 20 may illuminate the user's breath with infrared light having wavelength $\lambda 1$. When it is desired to detect the second target gas molecule, breath sensor 20 may illuminate the user's breath with infrared light having wavelength $\lambda 2$. When it is desired to detect the third target gas molecule, breath sensor 20 may illuminate the user's breath with infrared light having wavelength $\lambda 3$. When it is desired to detect the fourth target gas molecule, breath sensor 20 may illuminate the user's breath with infrared light having wavelength 4. When it is desired to detect the fifth target gas molecule, breath sensor 20 may illuminate the user's breath with infrared light having wavelength $\lambda 5$. Arrangements in which breath sensor 20 includes one or more infrared light detectors with optical filters having passbands that align with respective absorption lines of the desired target gas molecules may also be used.

Figure 6:
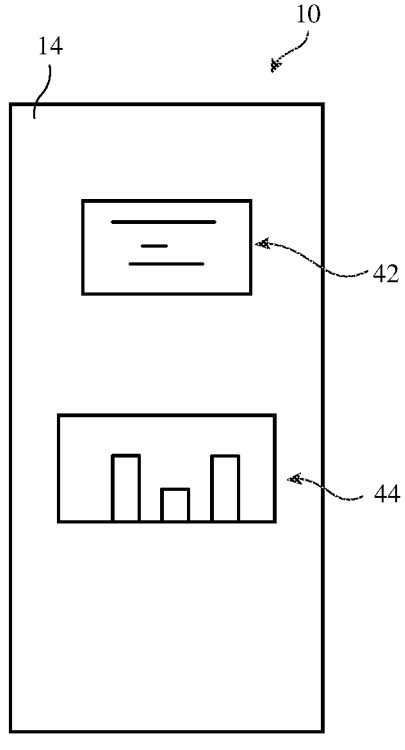
FIG. 6 is a front view of an illustrative electronic device having a display that may be used to convey breath sensing analysis results in accordance with an embodiment.

After analyzing the acquired breath sensor data, control circuitry 16 can take suitable action in response to the analysis results. FIG. 6 is a front view of device 10 showing how display 14 may display items 42 and 44 based on breath analysis results. For example, item 42 may include a message indicating that the user's breath suggests that the user has a metabolic disorder and should see a physician, that the user's breath suggests that the user is dehydrated and should drink water, that the user's breath shows signatures of garlic or onion and the user should use a mouthwash, etc. Item 44 may be a graph showing measured concentration levels of various target gases detected in the user's breath, a graph showing how a given health condition has changed over time based on breath analysis results, and/or other graphical information based on breath sensor measurements. The use of visual elements on display 14 to convey breath analysis information is merely illustrative. If desired, a speaker may be used to convey breath analysis information and/or a haptic output device may deliver haptic output based on breath analysis results.

Figure 7:
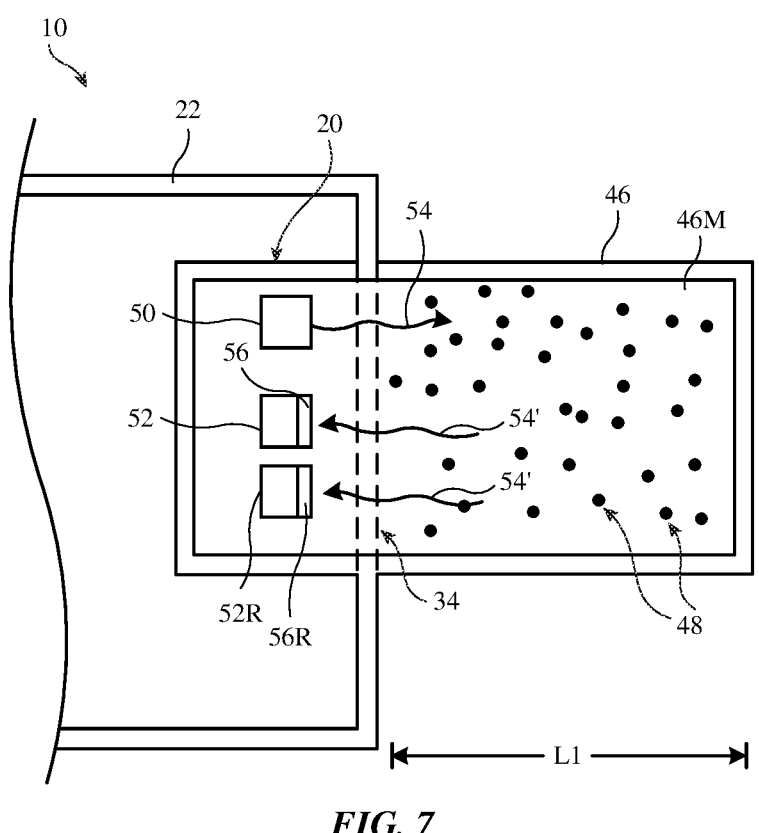
FIG. 7 is a cross-sectional side view of an illustrative electronic device having a non-dispersive infrared sensor that detects concentrations of one or more target breath gas molecules in a user's mouth in accordance with an embodiment.

FIG. 7 is a cross-sectional side view of an illustrative breath sensor in device 10 gathering breath sensor measurements from inside of a user's mouth, without the use of a nozzle, mouth-piece, or other separate enclosed chamber. Breath sensor 20 may be mounted behind sensor window 34 in housing 22. Sensor window 34 may be a single opening, two or more openings, an array of perforations, a gas-porous membrane, and/or other suitable window that allows passage of gas molecules such as gas molecules 48 in the user's breath.

Breath sensor 20 in device 10 may be a non-dispersive infrared sensor formed from one or more light-emitting elements such as light source 50 and one or more light detectors such as light sensors 52 and 52R. Light source 50 may include one or more light-emitting diodes (e.g., diodes formed from crystalline semiconductor dies, thin-film organic light-emitting diodes, etc.), one or more lasers, and/or other suitable types of light sources. Light detectors 52 and 52R may be photodiodes or other suitable light sensors. Light detector 52R may serve as a reference channel and may include an optical filter such as optical filter 56R. Optical filter 56R may have a passband that does not overlap any absorption lines of gas molecules (e.g., 4 microns or other suitable wavelength).

In some arrangements, light source 50 may be a broadband infrared light source that covers multiple absorption lines of different target gas molecules (e.g., a light source that emits infrared light spanning all of the wavelengths of FIG. 5). With this type of arrangement, light detector 52 may include an optical filter such as optical filter 56. Optical filter 56 may be configured to block light that does not fall within a narrow range of wavelengths that will be absorbed by a given target gas molecule to be detected. For example, if the target gas molecule has an absorption line at wavelength $\lambda 1$, optical filter 56 may be configured to transmit light having wavelength $\lambda 1$ while blocking other wavelengths of light (e.g., while blocking wavelengths $\lambda 2$, $\lambda 3$, $\lambda 4$, and $\lambda 5$). Arrangements in which filter 56 is tunable (e.g., so that filter 56 has a first passband in a first state, a second passband different from the first passband in a second state, etc.) may also be used.

In other arrangements, light source 50 may be a narrow band light source that emits infrared light across a narrow band of wavelengths (e.g., only covering one absorption line associated with the target gas molecule to be detected). For example, if the target gas molecule has an absorption line at wavelength $\lambda 1$, light source 50 may be configured to emit light that includes wavelength $\lambda 1$ without including other wavelengths of light (e.g., wavelengths $\lambda 2$, $\lambda 3$, $\lambda 4$, and $\lambda 5$). Arrangements in which light source 50 is tunable (e.g., so that light source 50 can emit light having a first wavelength such as wavelength $\lambda 1$ in a first state and emit light having a second wavelength such as wavelength $\lambda 2$ in a second state) may also be used.

Light sensors 52 and 52R may have one or more photodetectors. Photodetectors in light sensors 52 and 52R may be formed from separate semiconductor dies or may be formed on a common semiconductor die. In configurations in which sensor 52 contains multiple photodetectors, each photodetector may be sensitive to a different respective wavelength band associated with a respective target gas molecule absorption line (e.g., by including filters 56 with different passbands over the photodetectors). For example, light sensor 52 may include a first photodetector sensitive to wavelength $\lambda 1$ for detecting a first target gas molecule, a second photodetector sensitive to wavelength $\lambda 2$ for detecting a second target gas molecule, etc.

During breath sensor measurements, a user may place his or her face 46 in the vicinity of window 34 and may breath onto breath sensor 20. FIG. 7 shows no gap between face 46 and device 10, but this is merely illustrative. If desired, breath sensor measurements may be gathered even when a gap exists between face 46 and device 10. While mouth 46M is open, light source 50 may emit infrared light 54 into mouth 46M. Some of light 54 such as portions of light 54 having a wavelength that corresponds to an absorption line of the target gas molecule (e.g., wavelength $\lambda 1$, $\lambda 2$, $\lambda 3$, $\lambda 4$, or $\lambda 5$ of FIG. 5) will be absorbed by the target gas molecules 48. Other portions of light 54 may have a wavelength corresponding to an absorption line of the target gas molecule but will not be absorbed by the target gas molecule and will instead be reflected back to detector 52 as reflected light 54'. Portions of light 54 that do not have a wavelength corresponding to the absorption line of the target gas molecule will reflect back to detector 52 and reference detector 52R as reflected light 54'. Control circuitry 16 may then calculate the concentration of the target gas molecule using the Lambert-Beer law:

$$I = I_o e^{-\in lc} \tag{1}$$

In equation (1) above, I represents the intensity of reflected light 54' that has passed through target gas molecules 48 (e.g., I may be equal to the difference between the intensity of light detected by sensor 52 and reference sensor 52R), $I_0$ represents the initial intensity of light emitted from source 50, e represents the molar attenuation coefficient of the target gas molecule, c represents the concentration of the target gas molecule, and l is the light path length (e.g., two times the distance between sensor 20 and the point of reflection, such as the back of the inside of mouth 46M). Path length l may be predetermined (e.g., based on an estimated typical length to the back of a user's mouth) or may be measured (e.g., using a sensor 18 in device 10 such as an infrared depth sensor, a proximity sensor, or other sensor for measuring distances). For example, if a sensor in device 10 determines that the distance between sensor 20 and the back of mouth 46M is L1, then path length l may be equal to 2*L1. Control circuitry 16 may therefore solve for concentration c of a given target gas molecule based on the intensity of light emitted from source 50, the intensity of light detected by detectors 52 and 52R, the measured or estimated light path length l, and the molar attenuation coefficient of the target gas molecule.

In the example of FIG. 7, breath sensor 20 is analyzing breath coming from the user's mouth 46M. This is merely illustrative. If desired, breath sensor 20 may analyze breath coming from the user's nose. This type of arrangement is illustrated in FIG. 8.

Figure 8:
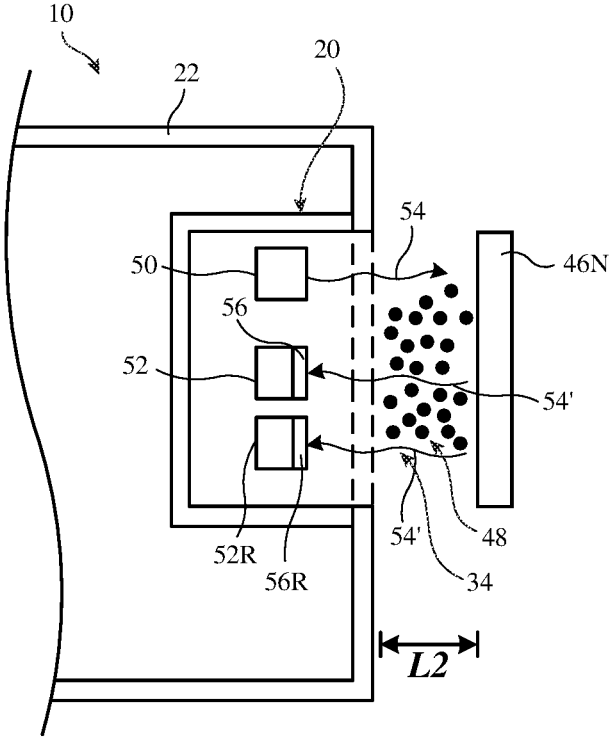
FIG. 8 is a cross-sectional side view of an illustrative electronic device having a non-dispersive infrared sensor that detects concentrations of one or more target breath gas molecules from a user's nose in accordance with an embodiment.

As shown in FIG. 8, breath sensor 20 may measure concentrations of target gas molecules in breath coming from the user's nose 46N. With this type of configuration, the user may breath through his or her nose 46N in the vicinity of window 34. Light source 50 may emit infrared light 54 towards nose 46N. Some of light 54 such as portions of light 54 having a wavelength that corresponds to an absorption line of the target gas molecule (e.g., wavelength $\lambda 1$, $\lambda 2$, $\lambda 3$, $\lambda 4$, or $\lambda 5$ of FIG. 5) will be absorbed by the target gas molecules 48. Other portions of light 54 may have a wavelength corresponding to an absorption line of the target gas molecule but will not be absorbed by the target gas molecule and will instead be reflected back to detector 52 as reflected light 54'. Portions of light 54 that do not have a wavelength corresponding to the absorption line of the target gas molecule will reflect back to detector 52 and reference detector 52R as reflected light 54'. A sensor 18 in device 10 such as a proximity sensor may be used measure the distance L2 between sensor 20 and the point of reflection on the user's face (e.g., the nose). Control circuitry 16 may then calculate the concentration of the target gas molecule using the Lambert-Beer law (equation (1) above), with the path length l equal to two times the distance L2 between sensor 20 and the point of reflection at the user's nose 46N.

Figure 9:
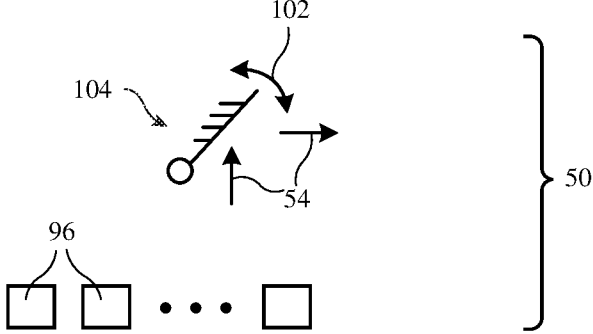
FIG. 9 is a diagram of an illustrative light source that may be used in a non-dispersive infrared sensor in accordance with an embodiment.

In some arrangements, it may be desirable to be able to steer the light beam emitted by light source 50 towards the user's mouth 46M (e.g., in arrangements where sensor 20 is analyzing breath from the user's mouth as in the example of FIG. 7) or towards the user's nose 46N (e.g., in arrangements where sensor 20 is analyzing breath from the user's nose as in the example of FIG. 8). Beam steerers may be formed from mirrors or other beam steering devices such as an optically phased array having an array of light sources with respective adjustable phases to control beam steering or adjustable diffractive optics such as electrically adjustable gratings. FIG. 9 shows an illustrative example in which light source 50 includes a mirror for steering the light beam from light source 50.

As shown in FIG. 9, light source 50 may include one or more light-emitting devices 96. Light-emitting devices 96 may be light-emitting diodes (e.g., diodes formed from crystalline semiconductor dies, thin-film organic light-emitting diodes, etc.), lasers, or other suitable light sources. Devices 96 may be formed on a common substrate (e.g. a common semiconductor die) or may be discrete components that are mounted on a common printed circuit (as examples). Devices 96 may include devices that operate at one or more different fixed wavelengths and/or may include one or more tunable light-emitting devices. Source 50 may include a single broadband light-emitting device 96 or may include one or more narrow band light-emitting devices 96 with each light-emitting device 96 emitting light that overlaps a respective absorption line of a given target gas molecule (e.g., a first light-emitting device 96 may emit light having wavelength $\lambda 1$ for detecting a first target gas molecule, a second light-emitting device 96 may emit light having wavelength $\lambda 2$ for detecting a second target gas molecule, etc.). If desired, devices 96 may be independently controlled, so that a single wavelength of light may be emitted at a time (if desired). In this way, adjustment of device(s) 96 may be used to adjust the wavelength of a light beam emitted from source 50.

Source 50 may include components for beam steering such as adjustable (scanning) mirror 104. Mirror 104 may be rotated in directions 102 (e.g., along two orthogonal axes) to steer the angular orientation of reflected emitted light beam 54 or other component adjustments may be made to steer the emitted beam. Using a system such as adjustable light source 50 of FIG. 9, emitted light attributes such as beam orientation (e.g., angular orientation) can be dynamically adjusted.

Figure 10:
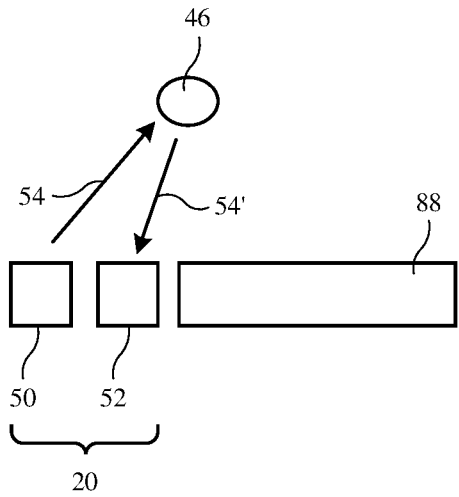
FIG. 10 is a diagram showing how a first sensor may gather information that helps steer a light beam in a second sensor during breath sensor measurements in accordance with an embodiment.

To ensure that breath sensor 20 gathers breath sensor measurements from the appropriate location on the user's face, information from one or more sensors 18 can be used to assist in beam targeting. Consider, as an example, the illustrative arrangement of FIG. 10. In the illustrative arrangement of FIG. 10, sensor 88 is used to gather data from the user's face 46.

Sensor 88 may be an image sensor (e.g., a two-dimensional and/or three-dimensional image sensor operating at infrared and/or visible light wavelengths), a proximity sensor, and/or other suitable sensor that can be used to determine the distance to or location of a particular region of interest such as the user's mouth. For example, sensor 88 may be a depth sensor that captures three-dimensional infrared depth maps of the user's face or a camera that captures visible images of the user's face. Control circuitry 16 may use image processing techniques such as pattern recognition techniques to analyze the captured image to determine the location of the user's face 46 and/or to determine suitable target locations within the user's face 46 (e.g., the user's mouth or nose) for directing light 54 from sensor 20. Pattern recognition may be performed on visible light images and/or infrared light images.

Once the location of the mouth or nose on face 46 is determined, a beam steerer in source 50 may be adjusted to direct a beam of light emitted from source 50 such as light beam 54 to face 46. Reflected light 54' that is reflected from face 46 (e.g., from the nose or from the back of the inside of the user's mouth) is measured by detector 52. During breath analysis, breath sensor 20 formed from source 50 and detector 52 may be adjusted. For example, wavelength can be adjusted (e.g., by selecting different light-emitting devices 96 within source 50 and/or by tuning an adjustable light-emitting device in source 50), beam orientation can be adjusted (e.g., using mirror 104 of FIG. 9 or other beam steering components), output power may be adjusted (e.g., based on signal strength feedback from the detector of the breath sensor), and/or other adjustments may be made to ensure that satisfactory data is gathered by breath sensor 20.

In addition to using an image sensor to obtain information that is used in steering beam 54 to a desired target region of the user's face, sensor 88 may include one or more additional sensors 18 for determining the path length traveled by light 54 (e.g., by measuring the distance between sensor 20 and the point of reflection of light 54 on the user's face and/or inside the user's mouth). These sensors may include, for example, distance or proximity sensors based on light, radio-frequency sensing, acoustic sensor components, or other distance sensors, may include three-dimensional image sensors that gather distance information and other location information, and/or other sensors.

In addition to or instead of using information from sensor 88 to steer light 54 from source 50 towards the appropriate location on the user's face, information from sensor 88 may be used to provide instructions to the user (e.g., visual instructions on display 14, audible instructions from a speaker, haptic-based instructions from a haptic output device, etc.) to instruct a user how to hold or angle device 10 relative to his or her face and/or how to move his or her face relative to device 10 during breath sensor measurements. For example, the user may be instructed to tilt device 10 and/or lift his or her chin to obtain better breath sensor measurements.

Following breath sensor measurements, some gas molecules may remain on breath sensor 20. Gas molecules that remain on breath sensor 20 can interfere with subsequent breath sensor measurements if care is not taken. To clear off gas molecules from breath sensor 20, device 10 may be subject to rapid movements, as shown in FIG. 11.

Figure 11:
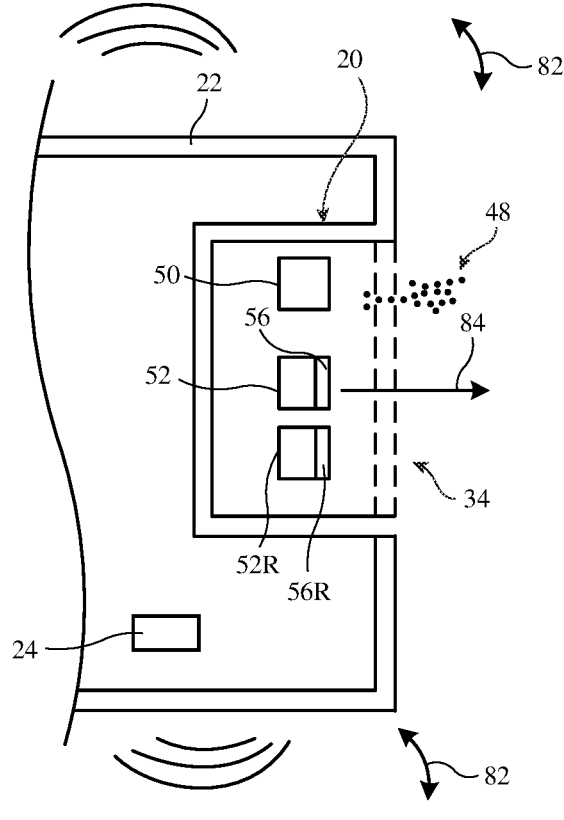
FIG. 11 is a cross-sectional side view showing how rapid movement of an electronic device may be used to clear gas molecules from a breath sensor in accordance with an embodiment.

As shown in FIG. 11, rapid movement of device 10 (e.g., in directions 82) helps to flush gas molecules 48 off of sensor 20 and out of device 10 via window 34 in direction 84. In some arrangements, the rapid movement of device 10 may be caused by a user holding device 10. For example, control circuitry 16 may use one or more output devices such as display 14, a speaker, or other output device to instruct a user to shake device 10 rapidly before and/or after a breath measurement.

In other arrangements, control circuitry 16 may use an actuator in device 10 such as actuator 24 to cause rapid movement of device 10 before and/or after a breath sensor measurement. Actuator 24 may be configured to move device 10 in one or more directions. For example, actuator 24 may laterally move device 10 and/or may rotate device 10 around one or more axes of rotation. If desired, multiple actuators 24 may be mounted in different locations of device 10. When driven by a control signal, actuator 24 may move (e.g., vibrate, pulse, tilt, push, pull, rotate, etc.) to cause device 10 to move or rotate in one or more directions. The movement may be slight (e.g., not noticeable or barely noticeable to a user of device 10), or the movement may be substantial. Actuator 24 may be based on one or more vibrators, motors, solenoids, piezoelectric actuators, speaker coils, or any other desired device capable of mechanically (physically) moving device 10.

Actuator 24 may be a dedicated actuator for clearing gas molecules from breath sensor 20 or actuator 24 may form part of a haptic output device that also provides haptic output to a user. For example, actuator 24 may include vibrators that are actuated to issue a haptic alert or notification to a user of device 10. Such alerts may include, for example, a received text message alert identifying that device 10 has received a text message, a received telephone call alert, a received email alert, an alarm notification alert, a calendar notification alert, or any other desired notification.

Figure 12:
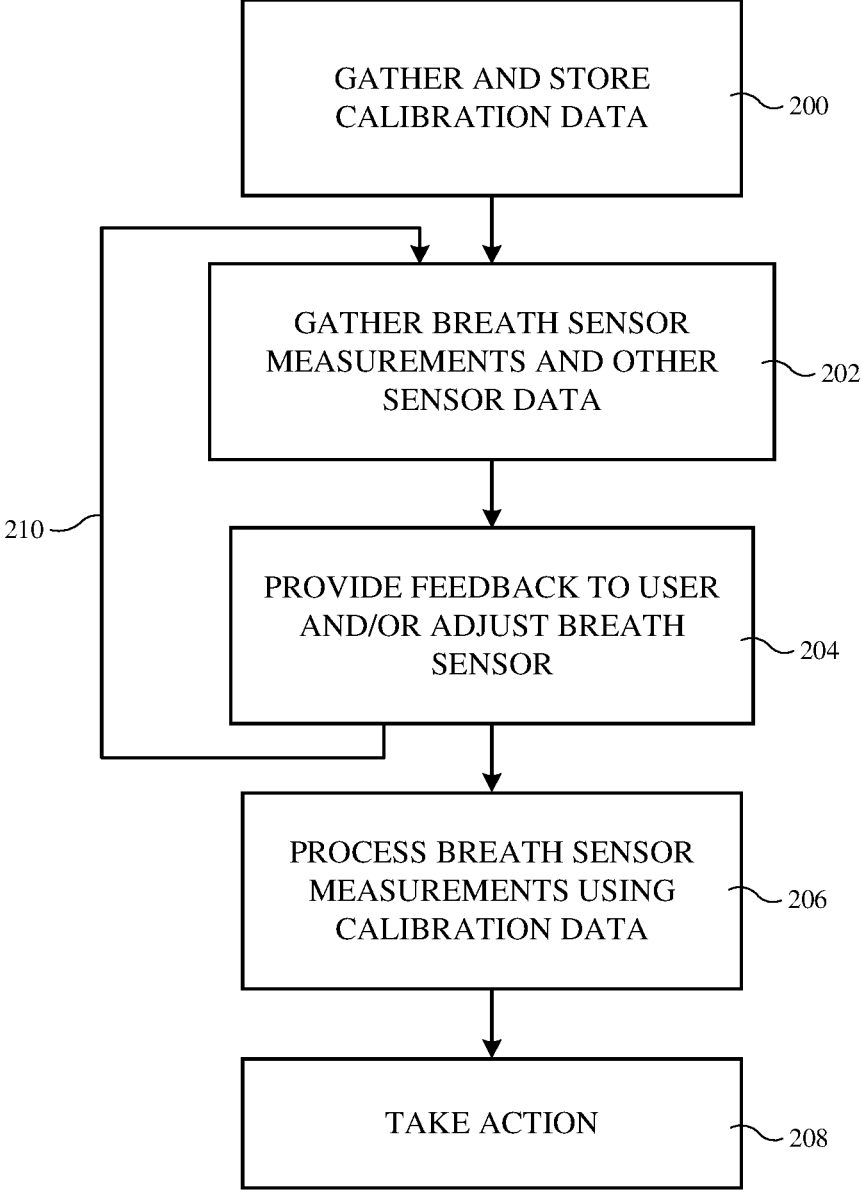
FIG. 12 is a flow chart of illustrative steps involved in breath analysis operations in accordance with an embodiment.

FIG. 12 is a flow chart of illustrative steps involved in using breath sensor 20 to conduct breath analysis.

During the operations of block 200, control circuitry 16 may gather calibration data which may be used to calibrate breath sensor 20. This may include, for example, capturing an infrared scan of the user's face, nose, lips, inside of the mouth, and/or other facial regions. Control circuitry 16 may illuminate different regions of the face with infrared light (e.g., from source 50 or from another suitable infrared light source in device 10) and may measure reflected infrared light using an infrared detector (e.g., detector 52 or other suitable infrared detector in device 10). This information may be used to obtain a map of baseline reflectance information across user's face, which in turn can be used to process breath sensor measurements. For example, facial hair may have an effect on the amount of infrared light that is reflected back from the user's face. By obtaining baseline infrared reflectance information from the user's face, this type of feature can be accounted for to ensure that breath analysis results are accurate.

If desired, other calibration data such as calibration data gathered during manufacturing may be stored in device 10. For example, breath sensor 20 may be exposed to different concentrations of a known test gas (e.g., nitrogen) without any presence of the desired target gas molecule (e.g., acetone). Using regression techniques (e.g., linear regression, least squares, etc.), calibration computing equipment may generate calibration data such as one or more coefficients that may be used to map future sensor output signals from breath sensor 20 to concentration levels. This calibration data may be stored in device 10 and used by control circuitry 16 to process measurements from breath sensor 20.

During the operations of block 202, breath sensor 20 may gather one or more measurements of the user's breath. This may include, for example, measuring breath from the user's mouth (e.g., as illustrated in FIG. 7) or measuring breath from the user's nose (e.g., as illustrated in FIG. 8). A user may place his or her face 46 in the vicinity of window 34 and may breath onto breath sensor 20. Breath sensor 20 may use source 50 to emit infrared light 54 towards the user's mouth and/or nose. Detector 52 (and reference detector 52R, if desired) may be used to detect an amount of reflected infrared light 54' that is not absorbed by the target gas molecule, as described in connection with FIGS. 7 and 8.

During the operations of block 202, one or more additional sensors may be used to provide additional information for breath sensing analysis. For example, sensor 88 of FIG. 10 may include a proximity sensor that measures a distance to the back of the inside of the user's mouth, to the user's nose, or to other suitable locations on the user's face where light from sensor 50 reflects back towards detector 52. This information may be used to determine the path length l traveled by light emitted from source 50 of sensor 20. Sensor 88 may additionally include one or more cameras (e.g., depth sensing infrared cameras, visible light cameras, etc.) configured to gather one or more images of the user's face or portions of the user's face. Control circuitry 16 may use image processing techniques such as pattern recognition techniques to analyze the captured image to determine the location of the user's face and to determine suitable target locations within the user's face (e.g., the user's mouth or nose). Pattern recognition may be performed on visible light images and/or infrared light images.

During the operations of block 204, control circuitry 16 may provide feedback to the user (e.g., visual feedback on display 14, audible feedback from a speaker, haptic feedback from a haptic output device, etc.) based on the breath sensor measurements and additional sensor data gathered during the operations of block 202. This may include, for example, providing instructions on how the user should hold or position device 10 and/or how the user should position his or her face for breath sensor measurements.

Instead of or in addition to providing feedback or instructions to the user, control circuitry 16 may adjust breath sensor 20. For example, control circuitry 16 may use beam steering components such as mirror 104 to steer the light beam emitted by source 50 in sensor 20 towards the appropriate location on the user's face (e.g., towards the nose, towards the inside of the mouth, etc.) based on the sensor data gathered during the operations of block 202. Additional adjustments to breath sensor 20 such as adjusting the wavelength of emitted light and/or adjusting the sensitivity of the detector to detect a different target gas molecule in the breath may also be made, if desired.

If adjustments are made during the operations of block 204 (e.g., position adjustments made by the user and/or sensor adjustments made by control circuitry 16 to sensor 20 to steer light towards the appropriate location on the user's face), processing may return to block 202 (see path 210 of FIG. 12) so that additional breath sensor measurements (and additional sensor data such as proximity sensor data, infrared image data, visible image data, other sensor data, etc.) may be gathered for processing by control circuitry 16.

During the operations of block 206, control circuitry 16 may analyze breath measurements from sensor 20 using the calibration data stored in device 10 (e.g., calibration data gathered during the operations of block 200 and/or calibration data gathered during manufacturing). This may include calculating the concentrations of one or more target gas molecules using the Lambert-Beer law (equation 1). Control circuitry 16 may solve for concentration c of a given target gas molecule based on the intensity of light 54 emitted from source 50, the intensity of light 54' detected by detectors 52 and 52R, the measured or estimated light path length l, and the molar attenuation coefficient of the target gas molecule.

Control circuitry 16 may also compare the detected concentrations of the target gas molecules with database information in order to make an assessment of one or more health conditions, as discussed in connection with FIG. 4. This may include, for example, comparing the concentration of a given target gas molecule (e.g., concentration value V1 of molecule M1, for example) with a threshold concentration (e.g., threshold concentration T1). If molecule M1 is a biomarker for a given disease or other health condition, control circuitry 16 may determine whether the given disease or other health condition is implicated (e.g., present or not present in the user) based on how measured concentration V1 compares to threshold concentration T1.

During the operations of block 208, control circuitry 16 may take suitable action based on the analysis results from block 206. Control circuitry 16 may output a breath analysis result based on how the user's breath information compares with the database information. The breath analysis result may include an assessment of a given health condition (e.g., whether the user has the given health condition and/or whether the user is at risk of having the given health condition), which may include providing a visual notification on display 14, providing an audio notification via one or more speakers in device 10, providing a haptic notification via one or more haptic output devices in device 10, updating a health-related application on device 10, logging the breath analysis results in a health-related application on device 10, transmitting the breath analysis results to an external electronic device and/or to a cloud-based location, providing recommendations, and/or taking other suitable actions. For example, if excess levels of acetone are detected in a user's breath, the user may be notified that the user is at risk of diabetes and should consult with a physician. Control circuitry 16 may output a message indicating that the user's breath suggests that the user has a metabolic disorder and should see a physician, that the user's breath suggests that the user is dehydrated and should drink water, that the user's breath shows signatures of garlic or onion and the user should use a mouthwash, etc. Control circuitry 16 may display a graph showing measured concentration levels of various target gases detected in the user's breath, a graph showing how a given health condition has changed over time based on breath analysis results, and/or other graphical information based on breath sensor measurements. In general, notifications can be issued, databases can be updated, recommendations may be provided, and/or other actions may be taken based on the results of the sensor processing operations of block 206. Notifications may include text notifications, audible alerts, email messages, other on-screen notification content, and/or other notification content.

Device 10 may gather and use personally identifiable information. It is well understood that the use of personally identifiable information should follow privacy policies and practices that are generally recognized as meeting or exceeding industry or governmental requirements for maintaining the privacy of users. In particular, personally identifiable information data should be managed and handled so as to minimize risks of unintentional or unauthorized access or use, and the nature of authorized use should be clearly indicated to users.

The foregoing is merely illustrative and various modifications can be made to the described embodiments. The foregoing embodiments may be implemented individually or in any combination.

Table of Reference Numerals

| 10 | electronic device |
|---|---|
| 12 | input-output devices |
| 14 | display |
| 16 | control circuitry |
| 18 | sensors |
| 20 | breath sensor |
| 22 | housing |
| 24 | actuator |
| F | front face |
| 34 | window |
| 36 | electrical components |
| 38 | printed circuit |
| M1, M2, M3 | molecules |
| V1, V2, V3 | concentration values |
| T1, T2, T3 | threshold values |
| 40 | breath sensor data |
| P1, P2, P3, P4, P5 | curves |
| 42, 44 | displayed items |
| 46 | face |
| 46M | mouth |
| 46N | nose |
| 48 | gas molecules |
| 50 | light source |
| 52, 52R | light sensor |
| 54, 54' | light |
| 56 | optical filter |
| L1, L2 | distances |
| 82, 84, 102 | directions |
| 88 | sensor |
| 96 | light-emitting devices |
| 104 | mirror |
| 200, 202, 204, 206, 208 | blocks |
| 210 | path |

What is claimed is:

1. An electronic device, comprising:
a housing having a sensor window;
a display in the housing;
a breath sensor in the housing aligned with the sensor window that gathers breath measurements using light;
a sensor that is used to measure a path length traveled by the light;
control circuitry configured to determine a concentration of a target breath gas molecule based on the breath measurements from the breath sensor and the path length.

2. The electronic device defined in claim 1 wherein the light comprises infrared light and wherein the breath sensor comprises:
a light source that emits the infrared light through the sensor window; and
a light detector that detects the infrared light after the infrared light passes through a volume containing the target breath gas molecule.

3. The electronic device defined in claim 2 wherein the light source comprises a broadband light source.

4. The electronic device defined in claim 3 wherein the light detector has an optical filter having a passband that overlaps an absorption line of the target breath gas molecule.

5. The electronic device defined in claim 2 wherein the light source comprises a narrow band light source having a wavelength that corresponds to an absorption line of the target breath gas molecule.

6. The electronic device defined in claim 2 wherein the breath sensor comprises a beam steerer for steering the infrared light.

7. The electronic device defined in claim 6 further comprising a camera that captures an image of a face, wherein the control circuitry uses the beam steerer to steer the infrared light towards a target location based on the image of the face.

8. The electronic device defined in claim 1 wherein the target breath gas molecule is a biomarker for a given health condition and wherein the control circuitry compares the concentration of the target breath gas molecule with database information to make an assessment of the given health condition.

9. The electronic device defined in claim 8 wherein the target breath gas molecule is selected from the group consisting of: carbon dioxide, acetone, ammonia, and nitric oxide.

10. The electronic device defined in claim 8 wherein the control circuitry uses the display to display breath analysis results, wherein the breath analysis results include the assessment of the given health condition.

11. The electronic device defined in claim 1 wherein the sensor comprises a proximity sensor.

12. An electronic device, comprising:
a housing having a sensor window;
a sensor that measures distance information;
a breath sensor that gathers breath measurements through the sensor window, comprising:
an infrared light source that emits infrared light through the sensor window; and
an infrared light detector that detects the infrared light after the infrared light passes through breath containing a target gas molecule that is a biomarker for a given health condition, wherein the distance information includes a distance traveled by the infrared light; and
control circuitry that analyzes the breath measurements from the breath sensor and the distance information from the sensor to determine if a user has the given health condition.

13. The electronic device defined in claim 12 wherein the control circuitry analyzes the breath measurements from the breath sensor to determine a concentration of the target gas molecule in the breath.

14. The electronic device defined in claim 12 wherein the infrared light source comprises a broadband infrared light source and wherein the infrared light detector has an optical filter with a passband that overlaps an absorption line of the target gas molecule.

15. The electronic device defined in claim 12 wherein the infrared light source comprises a narrow band infrared light source having a wavelength that corresponds to an absorption line of the target gas molecule.

* * * * *